United States Patent [19]

Tocker

[11] 4,235,872
[45] Nov. 25, 1980

[54] MICROENCAPSULATED METHOMYL INSECTICIDE

[75] Inventor: Stanley Tocker, Wilmington, Del.

[73] Assignee: E. I. Du Pont de Nemours and Company, Wilmington, Del.

[21] Appl. No.: 45,412

[22] Filed: Jun. 4, 1979

[51] Int. Cl.$^3$ .............................................. A61K 9/50
[52] U.S. Cl. ...................................... 424/19; 422/32; 422/33
[58] Field of Search .................. 424/19, 22, 32, 33

[56] References Cited

U.S. PATENT DOCUMENTS

| | | | |
|---|---|---|---|
| 3,074,845 | 1/1963 | Geary | 424/19 |
| 3,269,900 | 8/1966 | Rubin | 424/19 |
| 3,516,941 | 6/1970 | Matson | 424/32 |
| 3,575,882 | 4/1971 | Vandegaer et al. | 424/32 |
| 3,959,464 | 5/1976 | De Savigny | 424/32 |
| 4,056,610 | 11/1977 | Barber et al. | 424/32 |
| 4,107,292 | 8/1978 | Nemeth | 424/32 |
| 4,155,741 | 5/1979 | Scher et al. | 424/32 |
| 4,157,983 | 6/1979 | Golden | 424/32 |

FOREIGN PATENT DOCUMENTS 2805050 8/1978 Fed. Rep. of Germany .

OTHER PUBLICATIONS

Chem. Abstracts Index, vol. 89, Jul.–Dec. 1978 to vol. 66 (1967) entry "Methomyl".
C. A. 89, #175044g (1978) 88, #147388h (1978) 85, #73366p (1976) 84, #85650u (1976) 83, #127443r (1975).
C. A. 81, #34495c (1974) 80, #141773t (1974) 79, #14455v (1973).
Bakan, "Microcapsule Drug Delivery Systems", vol. 8, pp. 213–235 (1975) Polymer Science and Technology, Polymers in Medicine and Surgery.

*Primary Examiner*—Shep K. Rose

[57] ABSTRACT

Slow release insecticide microcapsules having a core of methomyl surrounded by a cover of allaromatic, uncrosslinked polyurea.

4 Claims, No Drawings

MICROENCAPSULATED METHOMYL INSECTICIDE

BACKGROUND OF THE INVENTION

This invention relates to insecticide microcapsules and, more particularly, to the microencapsulation of methomyl, 5-methyl-N-[(methylcarbamoyl)oxythioacetamide] to form a controlled release microcapsule.

Although methomyl is an important broadspectrum insecticide for use on many vegetables, field crops, fruit crops and ornamentals, it can decompose in as few as three days after application, depending on the field conditions, and can be phytotoxic to some plants, e.g., cotton, under certain conditions. Thus, efforts have been directed to developing techniques to improve the field performance of methomyl. Among general methods of microencapsulation most closely related to the process of the present invention are the following:

British Pat. No. 1,371,179, discloses a process for encapsulating water-immiscible material within a polymer shell which involves dispersing a water-immiscible phase that contains at least one organic polyisocyanate in an aqueous phase at a temperature of 20° to 90° C. to achieve hydrolysis-polymerization-encapsulation.

British Pat. No. 1,513,225 teaches that the polymer capsules of British Pat. No. 1,371,179 can be treated with ammonia or amines to remove unreacted isocyanate.

U.S. Pat. No. 3,959,464, alternatively, teaches the preparation of microcapsules of methyl or ethyl parathion contained within a wall of cross-linked polyamide-polyurea prepared in aqueous media.

None of these processes are practical for methomyl because methomyl exhibits poor solubility in the monomers used and a high solubility in water, especially at elevated temperatures e.g. as employed in British Pat. No. 1,371,179. In order to obtain high concentrations of methomyl in microcapsules, it is necessary that the material be retained in the organic dispersed phase until the polymer skin is formed.

SUMMARY OF THE INVENTION

This invention relates to a controlled release insecticide microcapsule consisting essentially of a core of methomyl surrounded by a cover of non-crosslinked, all-aromatic polyurea.

This invention also relates to a process for preparing controlled release microcapsules of methomyl comprising the steps of dispersing a solution of methylene chloride, methomyl and toluene-2,4-diisocyanate in aqueous medium to form a dispersion of liquid microspheres of methomyl, hardening the liquid microspheres by adding aqueous alkali to the dispersion at a temperature below about 20° C., to form microcapsules to which various formulating aids can be added. The resultant microcapsule dispersion can be applied to field crops as such or, preferably, purified before use. Purification is achieved by removing the methylene chloride, filtering, washing with water and drying for subsequent formulation. Surprisingly, the methylene chloride can be removed from the microcapsules by using an air stream or with vacuum evaporation without releasing significant amounts of free methomyl. In the microcapsules prepared according to this invention, the methomyl core comprises at least 20%, preferably at least 30% by weight of the microcapsule.

DETAILED DESCRIPTION OF THE INVENTION

According to the present invention, the field performance of methomyl can be improved, i.e., phytotoxicity can be reduced and residual activity can be increased, by encapsulating the methomyl with a non-crosslinked, all aromatic polyurea cover. The microencapsulation is accomplished by first dispersing a solution of methylene chloride, methomyl and toluene-2,4-diisocyanate of at least 95% purity in aqueous medium containing a surfactant with rapid initial stirring to form a dispersion of liquid microspheres about 5-150 microns, preferably 5-50 microns in diameter. In the most preferred embodiment of this invention, the microspheres are 5-30 microns in diameter as determined by visual examination under a microscope. The rate of initial stirring and concentration of surfactant or type determine the size of the liquid microspheres, a parameter which can be adjusted accordingly by those skilled in the art. Aqueous 0.25–1.0% poly(vinyl alcohol) such as Elvanol ® 50–42 (Du Pont) is the preferred surfactant, although others are operable.

The methylene chloride concentration can be about one to three times the weight of methomyl which is to be microencapsulated. In a preferred embodiment of this invention, the ratio of methylene chloride to methomyl is 2:1 by weight.

Optionally, the methylene chloride dispersed phase may also contain a polymer such as polystyrene and other additives which will stabilize the dispersion and product and will improve biological performance.

The ratio of toluene-2,4-diisocyanate to methomyl can be 1:4 to 3:1 by weight, but preferably the ratio is 1:1 to 1:2.

Other diisocyanates or mixtures thereof are not as effective in producing microspheres according to this invention. A commercial mixture of 80% toluene-2,4-diisocyanate and 20% toluene-2,6-diisocyanate (Hylene ® TM, Du Pont Co.) or methylene-p-phenyldiisocyanate, for example, will usually yield microspheres having less than 20% by weight methomyl after washing with water.

The liquid microspheres containing methomyl are hardened by adding an aqueous alkali to the dispersion at a temperature below about 20° C., preferably below about 10° C. The diisocyanate is partially hydrolyzed to amino groups followed by polymerization at the liquid microsphere-water interface to uncross-linked, all-aromatic polyurea.

Following polymerization, the methylene chloride can be removed by any suitable method, such as by air flow, vacuum or by hexane extraction. The remaining solution is filtered to recover the methomyl microcapsules; and, optionally, they can be washed with water and dried. In some applications where it may be desirable to have some free methomyl present, such as where extremely rapid insecticidal action is required, the washing step can be omitted.

The ratio of aqueous alkali or other alkali base or tertiary amine to toluene-2,4-diisocyanate is 0.25:2 to 2:1 on a molar basis. Sodium hydroxide is the preferred alkali, and it should be added to the dispersion in aqueous solution rapidly to harden the methomyl microspheres as quickly as possible. Other suitable bases include potassium and calcium hydroxide, and organic triamines such as triethylamine.

The following examples illustrate the present invention. Unless otherwise indicated, all temperatures are in °C. and all parts are by weight. Also, Elvanol ® 50-42 (E. I. du Pont de Nemours & Co.) is the surfactant poly(vinyl alcohol), which was prepared for use as a 0.5% by weight aqueous solution.

EXAMPLE 1

Aqueous Elvanol ® 50-42 (0.5%) was cooled to 5° and a solution of 20 g methylene chloride, 10.0 g methomyl and 5.0 toluene-2,4-diisocyanate (Hylene ® T, Du Pont Co.) was added with stirring. The stirring rate was adjusted by periodic examination under the microscope to give liquid microspheres of approximately $25\mu$ in diameter. Then a solution of 1.1 g sodium hydroxide in 10 ml. of water was added. The mixture was stirred while maintaining a temperature of 5°-11° for 1.5 hours, and then an air flow was applied for 3.0 hours with moderate stirring to remove methylene chloride. The resultant microcapsules were filtered off, washed with two 100 ml portions of water to remove unencapsulated methomyl and dried in an air flow to give 11 g of product, $20-30\mu$ in diameter, containing 50% methomyl as determined by extraction with refluxing methanol.

EXAMPLE 2

Example 1 was repeated except for the use of 33 g of methylene chloride solution containing 5% polystyrene (Shell 314). The resultant microspheres weighed 10.1 g, were $25-30\mu$ in diameter, and contained 46.5% by weight methomyl as determined by extraction with refluxing methanol.

EXAMPLE 3

Example 1 was carried out using the following solutions and modifications:
a. 650 ml 0.5% Elvanol ® 50-42
b. a solution of 400 g methylene chloride, 100 g toluene-2,4-diisocyanate and 200 g methomyl
c. a solution of 22 g sodium hydroxide in 50 ml of water.

The reaction temperature was 10° and a 3.5 hour reaction period was used before applying the air flow overnight. Washing involved successively 1000 ml $H_2O$ and two 500 ml washings. The dried product (131 g) consisted of $20-25\mu$ spheres which contained 43% by weight methomyl determined as in Examples 1 and 2.

The microcapsules of this invention are useful in agriculture for the control of insects which are controlled by methomyl. The insects are controlled by applying microcapsules to the locus of infestation, to the area to be protected, or to the pests themselves. For the control of insects on agricultural crops, the microcapsules are generally applied to the foliage or other plant parts which are infested or which are to be protected. Effective amounts to be applied depend upon the species to be controlled, its life stage, its size and location, the amount of rainfall, the time of year, moisture, temperature, type of application, plant spacing, and other variables. In general, 0.05 to 10 kg of active ingredient per ha may be required for insect control in agriculture with rates of 0.15 to 5 kg/ha usually being sufficient. In large-scale field operations, rates in the range of 0.25 to 3 kg/ha are generally used.

The microcapsules of this invention can be mixed with fungicides, bactericides, acaricides, as well as nematicides, unencapsulated methomyl, insecticides, or other biologically active compounds in order to achieve desired results with a minimum expenditure of time, effort and material. Amounts of these biologically active materials added for each part by weight of the composition of this invention may vary from 0.05 to 25 parts by weight.

The methomyl microcapsules of this invention possess significant advantages over prior art compounds. For example, their improved residual insecticidal activity can reduce the need for closely spaced multiple applications resulting in greater economy to the grower and dissemination of less pesticide in the environment. There is also less chance that the pesticide applied in this manner will be damaging to plants. A specific advantage of this type is the reduced side-effect on cotton. Treated leaves remain green and free of the reddening that may result when the same pesticide is applied in other forms.

Useful formulations of the microcapsules described in the previous examples can be prepared as wettable powders or aqueous suspensions in conventional ways. These formulations are sprayable and can be extended in suitable media and used at volumes of from a few pints to several hundred gallons per acre. High strength compositions are used primarily as intermediates for further formulation. The formulations, broadly, contain about 10% to 99% by weight of microcapsules and at least one of (a) about 1% to 20% surfactant(s) and (b) about 0% to 89% solid or liquid inert diluent(s). More specifically, they will contain these ingredients in the following approximate proportions:

|  | Percent by Weight* | | |
| --- | --- | --- | --- |
|  | Microcapsule | Diluent(s) | Surfactant(s) |
| Wettable Powder | 19-99 | 0-80 | 1-10 |
| Aqueous Suspensions | 10-60 | 30-89 | 1-20 |

*Weight of microcapsule plus at least one of a surfactant or diluent equals 100 weight percent.

Higher ratios of surfactant to active ingredient are sometimes desirable, and are achieved by incorporation into the formulation or by tank mixing.

Typical solid diluents are described in Watkins et al, "Handbook of Insecticide Dust Diluents and Carriers", 2nd Edn., Dorland Books, Caldwell, N.J. The more finely divided diluents are preferred for wettable powders. Water is the preferred liquid diluent but the formulation may contain other water-soluble materials such as alcohols, glycols or ketones to provide improved freeze resistance, for example, methanol, ethanol, propylene glycol, acetone, or the like. "McCutcheon's Detergents and Emulsifiers Annual", McCutcheon Division, MC Publishing Co., Ridgwood, N.J., as well as Sisely and Wood, "Encyclopedia of Surface Active Agents", Chemical Publishing Co., Inc. New York, 1964, list surfactants and recommended uses. All formulations can contain minor amounts of additives to reduce foam, caking, corrosion, microbiological growth, etc, or to buffer the pH.

The methods of making such compositions are well known. Fine solid compositions are made by blending.

Aqueous suspensions may be obtained directly from the encapsulation slurry without isolation of the dried microcapsules by warming and/or passing air or nitrogen through the slurry to remove methylene chloride. Any additionally desired diluents or surfactants may then be added.

Those skilled in the art of formulations will recognize that the above formulations are only examples of representative formulations and other product forms are possible.

In the following example ingredient proportions are by weight.

EXAMPLE 4

| Wettable Powder | |
| --- | --- |
| Methomyl microcapsules | 40% |
| Dioctyl sodium sulfosuccinate | 1.5% |
| Sodium lignin sulfonate | 3% |
| Low viscosity methyl cellulose | 1.5% |
| Attapulgite | 54% |

The ingredients are thoroughly blended and sifted through a U.S.S. No. 50 sieve (0.3 mm opening) before packaging. If desired all ingredients except the microcapsules may be ground in a hammer or fluid energy mill to reduce the particle size of these components. The microcapsules can then be blended into this ground premix.

EXAMPLE 5

The foliage of red kidney bean plants in the two-leaf stage was sprayed to run-off with dispersions of microcapsules of this invention at various concentrations. Dispersions were prepared by diluting appropiately weighed quantities of the active ingredient to 100 ml with water containing surface active agent (Duponol ® C, sodium lauryl sulfate, E. I. du Pont de Nemours & Co.) at 1:5000. After drying, the plants were placed under artificial light in a room maintained at 25°±2° C., 54±5% RH. Two days thereafter, leaves were excised from the plants and placed in covered 10 cm petri dishes along with moist filter paper to keep them fresh. Ten southern armyworm (Spodoptera eridania) larvae were placed in each dish. Tests were run in duplicate. The units were kept in a room maintained at 25±2° C., 54±5% RH. Mortality results were recorded two days thereafter. Seven days after the plants had been dried and placed in the relative humidity room, additional leaves were excised from the plants and tested in the same manner as those excised after two days.

TABLE 1

| Microcapsule Formulation | Methomyl Concentration in Spray % | % Larvae Dead | |
| --- | --- | --- | --- |
| | | 2 days | 7 days |
| Example 1 | 0.01 | 100 | 100 |
| | 0.005 | 100 | 95 |

TABLE 1-continued

| Microcapsule Formulation | Methomyl Concentration in Spray % | % Larvae Dead | |
| --- | --- | --- | --- |
| | | 2 days | 7 days |
| Example 2 | 0.01 | 100 | 95 |
| | 0.005 | 100 | 100 |
| Example 3 | 0.01 | 100 | 95 |
| | 0.005 | 100 | 100 |
| Untreated Control | — | 0 | 0 |
| Methomyl (unencapsulated) | 0.01 | 5 | 0 |

EXAMPLE 6

Potted cotton plants approximately 20 cm high having 2-3 true leaves were sprayed to run-off with aqueous dispersions of the following microcapsule formulations of this invention containing 500 ppm methomyl. The sprays contained surface active agent (Duponol ® C) at a concentration of 1:5000 water. Other sets of plants were similarly treated with methomyl. After drying, plants were set out in the greenhouse and held for observation.

TABLE 2

| Microcapsule Formulation (500 ppm methomyl) | Rating* (6 days) |
| --- | --- |
| Example 1 | 0.1 R |
| Example 2 | 0.1 R |
| Example 3 | 0 |
| Methomyl (unencapsulated) | 6 R |
| Untreated Control | 0 |

*"R" denotes typical methomyl effect, i.e., reddening of older leaves, slight puckering and black stippling of younger leaves. Rating is on the basis of 0 to 10, with 10 indicating total leaf area involvement.

What is claimed is:

1. An insecticide microcapsule consisting essentially of a core of methomyl surrounded by a cover of non-crosslinked, all aromatic polyurea formed by dispersing a solution of methylene chloride, methomyl and toluene-2,4-diisocyanate of at least 95% purity in aqueous medium creating a dispersion of liquid microspheres wherein the ratio of toluene-2,4-diisocyanate to methomyl is 1:4 to 3:1 by weight and the ratio of methylene chloride to methomyl is about 2:1 to 3:1 by weight, hardening the liquid microspheres by adding an aqueous alkali to the dispersion, the ratio of aqueous alkali to toluene-2,4-diisocyanate being about 0.25:2 to 2:1 on a molar basis, and removing the methylene chloride.

2. The insecticide microcapsule of claim 1 in which the core of methomyl comprises at least 30% by weight of the microcapsule.

3. The insecticide microcapsule of claim 1 or claim 2 which is from 5 to 150 microns in diameter.

4. The insecticide microcapsule of claim 3 which is from 5 to 50μ in diameter.

* * * * *